US012558503B2

(12) United States Patent
Rapoport et al.

(10) Patent No.: US 12,558,503 B2
(45) Date of Patent: Feb. 24, 2026

(54) BILEVEL RESPIRATORY THERAPY SYSTEM, CONTROLLER AND METHOD

(71) Applicant: NEW YORK UNIVERSITY, New York, NY (US)

(72) Inventors: David M. Rapoport, New York, NY (US); David Robin Whiting, Auckland (NZ)

(73) Assignee: NEW YORK UNIVERSITY, New York, NY (US)

( * ) Notice: Subject to any disclaimer, the term of this patent is extended or adjusted under 35 U.S.C. 154(b) by 1098 days.

(21) Appl. No.: 16/312,193

(22) PCT Filed: Jul. 6, 2017

(86) PCT No.: PCT/NZ2017/050091
§ 371 (c)(1),
(2) Date: Dec. 20, 2018

(87) PCT Pub. No.: WO2018/009078
PCT Pub. Date: Jan. 11, 2018

(65) Prior Publication Data
US 2019/0232005 A1     Aug. 1, 2019

Related U.S. Application Data

(60) Provisional application No. 62/436,683, filed on Dec. 20, 2016, provisional application No. 62/358,755, filed on Jul. 6, 2016.

(51) Int. Cl.
| | |
|---|---|
| *A61M 16/16* | (2006.01) |
| *A61M 16/00* | (2006.01) |
| *A61M 16/08* | (2006.01) |
| *A61M 16/10* | (2006.01) |

(52) U.S. Cl.
CPC ...... *A61M 16/024* (2017.08); *A61M 16/0003* (2014.02); *A61M 16/0069* (2014.02); *A61M 16/0875* (2013.01); *A61M 16/109* (2014.02); *A61M 16/1095* (2014.02); *A61M 16/16* (2013.01); *A61M 2016/0027* (2013.01); *A61M 2016/0036* (2013.01); *A61M 2016/0039* (2013.01); *A61M 16/0066* (2013.01); *A61M 2205/16* (2013.01); *A61M 2205/3653* (2013.01); *A61M 2205/50* (2013.01); *A61M 2230/42* (2013.01)

(58) Field of Classification Search
CPC ......... A61M 16/00; A61M 2016/0036; A61M 2205/16; A61M 2230/42; A61M 16/024; A61M 16/0069; A61M 16/1095; A61M 16/0875; A61M 16/16; A61M 2016/0027; A61B 5/08; A62B 7/00
See application file for complete search history.

(56) References Cited

U.S. PATENT DOCUMENTS

| | | | | | |
|---|---|---|---|---|---|
| 3,961,627 | A | * | 6/1976 | Ernst ................. | A61M 16/0009 128/204.21 |
| 5,303,698 | A | * | 4/1994 | Tobia .................. | A61M 16/024 128/204.21 |
| 6,502,572 | B1 | * | 1/2003 | Berthon-Jones ..... | A61B 5/4818 128/204.23 |
| 6,988,994 | B2 | * | 1/2006 | Rapoport .......... | A61M 16/0069 128/204.26 |
| 8,528,551 | B2 | * | 9/2013 | Mulcahy ............. | A61M 16/024 128/204.23 |
| 8,616,202 | B2 | * | 12/2013 | Tatkov .............. | A61M 16/0012 128/203.17 |
| 8,991,392 | B1 | * | 3/2015 | Whiting ............ | A61M 16/0069 128/204.23 |
| 9,205,215 | B2 | * | 12/2015 | McAuley .............. | A61M 16/06 |
| 9,220,865 | B2 | * | 12/2015 | Potharaju .......... | A61M 16/1095 |
| 9,999,742 | B2 | * | 6/2018 | Millar ................. | A61M 16/024 |
| 10,322,251 | B2 | * | 6/2019 | Rapoport .............. | A61M 16/06 |

(Continued)

FOREIGN PATENT DOCUMENTS

| | | | | |
|---|---|---|---|---|
| WO | WO-2011149362 A1 | * | 12/2011 | ........ A61M 16/0666 |
| WO | WO-2014186584 A2 | * | 11/2014 | ......... A61M 16/024 |
| WO | WO 2015/150997 | | 10/2015 | |

OTHER PUBLICATIONS

International Search Report, PCT/NZ2017/050091, dated Sep. 29, 2017; 5 pages.

*Primary Examiner* — Brandy S Lee
*Assistant Examiner* — Tyler A Raubenstraw
(74) *Attorney, Agent, or Firm* — Fay Kaplun & Marcin, LLP

(57) ABSTRACT

A respiratory therapy system is configured to supply breathing gases to a patient and comprises a controller configured to control the pressure of breathable gas delivered to the patient. The system can control the flow of breathable gas to the patient taking into account whether or not a breath is detected, and whether or not the patient is awake or asleep. The system is configured to: detect when the patient is inhaling and to control the flow generator to deliver breathable gas at an inspiration pressure (IPAP), detect when the patient is exhaling and to control the flow generator to deliver breathable gas at an expiration pressure (EPAP), the EPAP being lower than the IPAP, and detect when the patient is at least one of awake and/or asleep. The system is also configured to receive or generate a back-up time related variable which is compared with a time related variable of at least a portion of a breath of the patient such that the breathable gas delivered to the patient is automatically controlled at IPAP, if inspiration is not detected in accordance with the back-up time related variable. The back-up time related variable may be a rate or duration for example. The delivery of breathable gas to the patient is further controlled if inspiration is not detected in accordance with the back-up time related variable and the system detects that the patient is awake. For example, if the patient is awake, the system may not automatically switch to IPAP, even if a breath is not detected within a predetermined time.

20 Claims, No Drawings

(56)                    References Cited

U.S. PATENT DOCUMENTS

| | | | | | |
|---|---|---|---|---|---|
| 10,342,942 | B2 * | 7/2019 | Tatkov | ............... | A61M 16/0875 |
| 10,406,306 | B2 * | 9/2019 | Whiting | ............ | A61M 16/0069 |
| 10,842,958 | B1 * | 11/2020 | Rapoport | ............ | A61M 16/024 |
| 2003/0062044 | A1 * | 4/2003 | Berthon-Jones | ............................ A61M 16/0875 128/204.18 |
| 2004/0016433 | A1 | 1/2004 | Estes et al. | | |
| 2004/0231670 | A1 * | 11/2004 | Bassin | ................. | A61M 16/20 128/204.18 |
| 2005/0076908 | A1 * | 4/2005 | Lee | ...................... | A61B 5/4809 600/544 |
| 2005/0256420 | A1 * | 11/2005 | Norman | ................. | A61B 5/087 600/533 |
| 2005/0268912 | A1 * | 12/2005 | Norman | ............... | A61M 16/10 128/204.23 |
| 2006/0000475 | A1 * | 1/2006 | Matthews | ........... | A61M 16/026 128/204.21 |
| 2006/0069326 | A1 * | 3/2006 | Heath | .................. | A61H 31/006 601/41 |
| 2006/0070624 | A1 * | 4/2006 | Kane | ................. | A61M 16/0003 128/204.23 |
| 2007/0032733 | A1 * | 2/2007 | Burton | ................. | A61B 5/7264 600/509 |
| 2007/0221224 | A1 * | 9/2007 | Pittman | ............... | A61M 16/209 128/204.22 |
| 2008/0127978 | A1 | 6/2008 | Rubin et al. | | |
| 2009/0107493 | A1 * | 4/2009 | Liu | ....................... | A61M 16/16 392/394 |
| 2010/0108066 | A1 * | 5/2010 | Martin | ............... | A61M 16/204 128/204.23 |
| 2011/0297155 | A1 * | 12/2011 | Shelly | ................. | A61M 16/024 128/204.23 |
| 2012/0010519 | A1 * | 1/2012 | Rapoport | ............... | A61B 5/087 128/204.23 |
| 2013/0066226 | A1 | 3/2013 | Baloa Welzien et al. | | |
| 2013/0247914 | A1 | 9/2013 | Truschel et al. | | |
| 2014/0116440 | A1 * | 5/2014 | Thompson | ............. | A61B 5/087 128/204.23 |
| 2014/0123977 | A1 | 5/2014 | LaLonde | | |
| 2014/0144438 | A1 * | 5/2014 | Klasek | ................. | A61B 5/4812 128/203.14 |
| 2015/0107594 | A1 * | 4/2015 | Rapoport | ............ | A61B 5/4812 128/204.23 |
| 2015/0128942 | A1 * | 5/2015 | Tatkov | .............. | A61M 16/0003 128/203.14 |
| 2015/0265789 | A1 * | 9/2015 | Whiting | ............... | A61B 5/4836 128/204.23 |
| 2016/0101250 | A1 * | 4/2016 | Gradon | ................. | A61M 16/16 128/204.23 |
| 2016/0144148 | A1 * | 5/2016 | Crone | .................... | G16H 40/63 128/203.14 |
| 2017/0348498 | A1 * | 12/2017 | Salter | ................... | A61B 5/4833 |
| 2018/0221608 | A1 * | 8/2018 | Schwaibold | ........ | A61M 16/024 |
| 2018/0236191 | A1 * | 8/2018 | Martin | .................. | A61M 16/08 |
| 2019/0224431 | A1 * | 7/2019 | Kwok | .............. | A61M 16/0066 |

* cited by examiner

BILEVEL RESPIRATORY THERAPY SYSTEM, CONTROLLER AND METHOD

BACKGROUND OF THE INVENTION

Field of the Invention

The present invention generally relates to a bi-level respiratory therapy system, controller and method wherein pressure of a breathable gas delivered to a patient is controlled to increase during inspiration and to decrease during expiration.

Description of the Related Art

Respiratory therapy systems, controllers and methods have been proposed to treat respiratory illness, including, for example, Obstructive sleep apnea (OSA).

OSA is associated with many conditions in which there is an anatomic or functional narrowing of the patient's upper airway, and is characterized by an intermittent obstruction of the upper airway occurring during sleep. The obstruction results in a spectrum of respiratory disturbances ranging from the total absence of airflow (apnea) to significant obstruction with or without reduced airflow (hypopnea and snoring), despite continued respiratory efforts. The morbidity of the syndrome arises from hypoxemia, hypercapnia, bradycardia and sleep disruption associated with the apneas and subsequent arousals from sleep.

Positive airway pressure (PAP) therapy has become the mainstay of treatment in Obstructive Sleep Disordered Breathing (OSDB), which includes Obstructive Sleep Apnea, Upper Airway Resistance Syndrome, Snoring, exaggerations of sleep induced increases in the collapsibility of the upper airway and all conditions in which inappropriate collapsing of a segment of the upper airway causes significant un-physiologic obstruction to airflow. This collapse generally occurs whenever pressure in the collapsible portion of the airway decreases below a level defined as a "critical tissue pressure" in the surrounding wall. The PAP therapy is directed to maintaining pressure in the collapsible portion of the airway at or above the critical tissue pressure at all times. It is well known during PAP therapy to increase the pressure delivered to the patient's airway to a level higher than this critical tissue pressure at all times when the patient is wearing the device. In general, the need for the PAP therapy occurs only during sleep. In most cases, PAP therapy does not take the sleep/wake state of the patient into account, such that PAP systems can apply pressure unnecessarily when the patient is awake. The applied pressure is either a constant pressure, or a pressure based on breath-by-breath determination of the need for treatment. In some cases the sleep/wake state of the patient is taken into account in some respects.

SUMMARY OF THE DISCLOSURE

The present disclosure relates to a bi-level respiratory therapy system, controller and method, and/or that will at least provide the public or the medical profession with a useful choice.

Accordingly in one aspect the invention may broadly be said to consist in a respiratory therapy system configured to supply breathing gases to a patient, the system comprising a controller configured to control the pressure of breathable gas delivered to the patient by a flow generator and to receive one or more signals from one or more sensors indicative of the pressure and/or flow of the gas in the system, wherein the system is configured to:

- detect when the patient is inhaling and to control the flow generator to deliver breathable gas at an inspiration pressure (IPAP),
- detect when the patient is exhaling and to control the flow generator to deliver breathable gas at an expiration pressure (EPAP), the EPAP being lower than the IPAP,
- detect when the patient is at least one of awake and/or asleep, the system further comprising, or being configured to receive or generate a back-up time related variable;
- the system being further configured to compare a time related variable of at least a portion of a breath of the patient with the back-up time related variable and to automatically control the flow generator to deliver breathable gas to the patient at IPAP, if inspiration is not detected in accordance with the back-up time related variable,
- the system being further configured to further control the delivery of breathable gas to the patient if inspiration is not detected in accordance with the back-up time related variable and the system detects that the patient is awake.

The back-up time related variable may be a back-up duration in the sense of a length of time of a breathing parameter. For example, the back-up time related variable may be a time period which is set to be longer than the length of a complete breath of the patient, such as between 2 and 10 seconds for example.

The system may therefore, in some examples, be configured to control the delivery of breathable gas so that IPAP is not delivered to the patient if inspiration is not detected after the back-up time duration and the system detects that the patient is awake. The back-up duration is any one or more of:

- a) greater than the length of all of, or a portion of, a breath of a patient;
- b) less than the length of all of, or a portion of, a breath of a patient;
- c) substantially the same as the length of all of, or a portion of, a breath of a patient.

The back-up duration may be proportional to, or calculated in accordance with, the duration of the expiratory portion of the breath of a patient.

The length of all of, or a portion of, a breath of a patient may be the maximum length that is measured in a given sampling period. For example the maximum breath might be the longest breath that is detected over five to ten sample breaths.

The back-up time related variable may be a back-up rate in the sense of a frequency at which a breathing parameter occurs, or at which complete breaths occur. For example, the back-up time related variable may be the rate at which complete breaths occur. The back-up time related variable may be the rate expressed in complete breaths per minute (BPM), such as between 6 to 30 BPM and preferably 10 to 20 BPM. The system may therefore be configured to control the delivery of breathable gas so that IPAP is not delivered to the patient if inspiration is not detected after the back-up time frequency and the system detects that the patient is awake. Thus for example, the if the patient is breathing at a rate of 10-12 BPM, but this drops to 7-8 BPM, the system may be configured to deliver IPAP, if the system also detects that the patient is asleep.

The back-up rate may be:

a) less than the minimum frequency of all of, or a portion of, a breath of a patient;

b) greater than the minimum frequency of all of, or a portion of, a breath of a patient;

c) substantially the same as the maximum frequency of all of, or a portion of a breath of a patient.

The back-up time related variable may be calculated or otherwise determined in respect of a typical or average breath of the patient, or the inspiratory or expiratory portion of a typical or average breath.

The system may be operative according to a spontaneous mode (S-mode), in which the flow generator delivers breathable gas at an inspiration pressure (IPAP) on detection of inspiration, and at a lower expiratory pressure (EPAP) on detection of expiration. In S-mode, triggering of the change in pressure from EPAP to IPAP may be based only on the detection of patient inspiration. Typically, there may be a maximum duration for which IPAP can last, such that the system will not continue to deliver IPAP in the event of a leak.

The system may be operative according to a spontaneous/timed mode (S/T mode) in which detection of a phase or portion of a patient breath may trigger the change between EPAP and IPAP, but additionally a back-up breath is applied by the system if inspiration is not detected within a back-up duration or in accordance with a back-up rate. Typically, the back-up duration or back-up rate may be set by a clinician. The back-up breath will typically have a set duration ($D_{set}$) such that when the back-up breath is triggered, IPAP will be applied for $D_{set}$.

The system may be operative to disable or disengage or override the back-up time related variable if the system detects that the patient is awake. In one example, the system may be configured to control the delivery of breathable gas to the patient such that if the system detects that the patient is awake, IPAP is provided only on detection of inspiration or the onset of inspiration, and not as a result of the back-up time related variable. In other words, the system is configured to provide S/T mode while the patient is asleep and S-mode while the patient is awake. Alternatively IPAP is provided only due to being triggered by patient breathing.

In a further example, the system may be configured to control the delivery of breathable gas to the patient such that IPAP is not provided if the system detects that the patient is awake. That is, bi-level therapy using IPAP and EPAP may be provided if the system detects that the patient is asleep, and constant pressure (known as continuous positive airway pressure or CPAP) may be provided when the system detects that the patient is awake. The CPAP may be lower than the IPAP, and is preferably also lower than the EPAP. The CPAP may be lower than a therapeutic pressure, and is preferably lower than 4 cm $H_2O$. The CPAP may be set by a clinician or selectable by a user, or determined by the system.

The system may be operative to adjust the back-up time related variable if the system detects that the patient is awake. In one example the back-up time related variable is a back-up duration, wherein the length of the back-up duration may be increased if the system detects that the patient is awake, such that the back-up duration is longer than the typical length of a breath of the patient. In other words, the back-up duration may be shorter when the patient is asleep and longer when the patient is awake. In another example the back-up time related variable may be a back-up rate or frequency, where the back-up rate or frequency is decreased if the system detects that the patient is awake, such that the back-up rate is slower than the typical breathing rate of a patient.

The system may be configured such that IPAP and/or EPAP delivered to the patient are lower when the system detects that the patient is awake than IPAP and/or EPAP when the system detects that the patient is asleep. Lowering IPAP and/or EPAP when the patient is awake may increase comfort by not subjecting the patient to high therapeutic pressures. In contrast some patients might be used to the higher pressures that are delivered when the patient is asleep and might find the lower pressures uncomfortable.

The system may be configured such that a pressure difference between IPAP and EPAP is different when the system detects that the patient is awake as compared to when the patient is asleep. In one example, the pressure difference may be greater when the patient is awake, for example to improve patient comfort during expiration.

The system may be configured such that a maximum ($D_{-max}$) duration or set ($D_{set}$) duration that the system provides IPAP to the patient is varied when the system detects that the patient is awake. For example $D_{set}$ could be used where the back-up time related variable is a back-up rate. In some examples, the maximum or set duration of IPAP may be disabled. In some examples, the maximum or set duration of IPAP may be increased. The system may be configured such that $D_{-max}$ could be overridden, either automatically by the system or by a system operator, when the patient is awake, to make it more comfortable if a patient takes an extra deep breath. Such functionality may help to avoid the patient being uncomfortable if the pressure drops due to $D_{-max}$, while the patient is still inhaling while awake.

The system may be configured such that the IPAP and/or EPAP pressure support supplied to the patient when the patient is asleep is varied as compared to the IPAP and/or EPAP pressure support supplied to the patient when the patient is awake. In some examples, the pressure support may be reduced when the patient is asleep to provide a comfort feature in some patient groups such as obstructive sleep apnea (OSA). In some examples, the pressure support may be increased when the patient is asleep. This may be useful for patients having obesity hypoventilation syndrome (OHS) to increase ventilation when they are hypoventilating while asleep.

The system may comprise, in addition to the controller, any one or more of the following:

a) a flow generator such as a blower or pressurised gas source;

b) a humidifier to heat the breathable gas delivered to the patient;

c) a gas delivery tube between the flow generator and the patient, where the tube may be heated; and/or d) a patient interface configured to provide a seal with the face of the patient and to receive gas from a gas delivery tube.

The system may be further configured to further control the delivery of breathable gas to the patient if inspiration is not detected in accordance with the back-up time related variable and the system detects that the patient is awake such that CPAP is delivered to the patient. The CPAP may be lower than the IPAP and/or the EPAP.

The system may be further configured to further control the delivery of breathable gas to the patient if inspiration is not detected in accordance with the back-up time related variable and the system detects that the patient is awake such that IPAP is delivered to the patient, when the patient is awake.

The system may be further configured to further control the delivery of breathable gas to the patient if inspiration is not detected in accordance with the back-up time related variable and the system detects that the patient is awake such that the back-up time related variable when the patient is awake is different from when the patient is asleep.

According to a further aspect of the invention there is provided a controller for a respiratory therapy system configured to supply breathing gases to a patient, the controller being configured to control the pressure of breathable gas delivered to the patient by a flow generator and to receive one or more signals from one or more sensors indicative of the pressure and/or flow of the gas in the system, wherein the controller is configured to:

detect when the patient is inhaling and to control the flow generator to deliver breathable gas at an inspiration pressure (IPAP), detect when the patient is exhaling and to control the flow generator to deliver breathable gas at an expiration pressure (EPAP), the EPAP being lower than the IPAP, detect when the patient is awake and/or asleep, to set, generate or receive a back-up time related variable;

the controller being further configured to compare a time related variable of at least a portion of the breath of the patient with the back-up time related variable and to automatically control the flow generator to deliver breathable gas to the patient at IPAP, if inspiration is not detected in accordance with the back-up time related variable, the controller being further configured to control the delivery of breathable gas to the patient if inspiration is not detected in accordance with the back-up time related variable and the system detects that the patient is awake.

According to another aspect of the invention there is provided a method of controlling a respiratory therapy system configured to supply breathing gases to a patient, the system comprising a controller configured to control the pressure of breathable gas delivered to the patient by a flow generator and to receive one or more signals from one or more sensors indicative of the pressure and/or flow of the gas in the system, the method comprising steps of:

detecting when the patient is inhaling and to control the flow generator to deliver breathable gas at an inspiration pressure (IPAP), detecting when the patient is exhaling and to control the flow generator to deliver breathable gas at an expiration pressure (EPAP), the EPAP being lower than the IPAP, detecting when the patient is awake and/or asleep, setting, generating or receiving a back-up time related variable;

comparing a time related variable of at least a portion of a breath of the patient with the back-up time related variable and automatically controlling the flow generator to deliver breathable gas to the patient at IPAP, if inspiration is not detected in accordance with the back-up time related variable, further controlling the delivery of breathable gas to the patient if both inspiration is not detected in accordance with the back-up time related variable and the system detects that the patient is awake.

According to another aspect the invention may broadly be said to consist in a respiratory therapy system configured to supply breathing gases to a patient, the system comprising a controller configured to control the pressure and/or flow of breathable gas delivered to the patient from a gas source, and to receive one or more signals from one or more sensors indicative of the pressure and/or flow of the gas in the system, wherein the system is configured to:

detect when the patient is inhaling and to control the system to deliver breathable gas at an inspiration pressure (IPAP), detect when the patient is exhaling and to control the system to deliver breathable gas at an expiration pressure (EPAP), the EPAP being lower than the IPAP, detect when the patient is at least one of awake and/or asleep, the system further comprising, or being configured to receive or generate a back-up time related variable;

the system being further configured to compare a time related variable of at least a portion of a breath of the patient with the back-up time related variable and to automatically control the system to deliver breathable gas to the patient at IPAP, if inspiration is not detected in accordance with the back-up time related variable, the system being further configured to further control the delivery of breathable gas to the patient if inspiration is not detected in accordance with the back-up time related variable and the system detects that the patient is awake.

According to another aspect the invention may broadly be said to consist in a respiratory therapy system configured to supply breathing gases to a patient, the system comprising a controller configured to control the pressure of breathable gas delivered to the patient by a flow generator and to receive one or more signals from one or more sensors indicative of the pressure and/or flow of the gas in the system, wherein the system is configured to:

detect when the patient is inhaling and to control the flow generator to deliver breathable gas at an inspiration pressure (IPAP), detect when the patient is exhaling and to control the flow generator to deliver breathable gas at an expiration pressure (EPAP), the EPAP being lower than the IPAP, detect when the patient is at least one of awake and/or asleep, the system further comprising, or being configured to receive or generate, a back-up duration;

the system being further configured to compare a duration of at least a portion of a breath of the patient with the back-up duration and to automatically control the flow generator to deliver breathable gas to the patient at IPAP, if inspiration is not detected in accordance with the back-up duration, the system being further configured to further control the delivery of breathable gas to the patient if inspiration is not detected in accordance with the back-up duration and the system detects that the patient is awake.

According to another aspect the invention may broadly be said to consist in a respiratory therapy system configured to supply breathing gases to a patient, the system comprising a controller configured to control the pressure of breathable gas delivered to the patient by a flow generator and to receive one or more signals from one or more sensors indicative of the pressure and/or flow of the gas in the system, wherein the system is configured to:

detect when the patient is inhaling and to control the flow generator to deliver breathable gas at an inspiration pressure (IPAP), detect when the patient is exhaling and to control the flow generator to deliver breathable gas at an expiration pressure (EPAP), the EPAP being lower than the IPAP, detect when the patient is at least one of awake and/or asleep,

7 the system further comprising, or being configured to receive or generate, a back-up rate;

the system being further configured to compare a rate of at least a portion of a breath of the patient with the back-up rate and to automatically control the flow generator to deliver breathable gas to the patient at IPAP, if inspiration is not detected in accordance with the back-up rate, the system being further configured to further control the delivery of breathable gas to the patient if inspiration is not detected in accordance with the back-up rate and the system detects that the patient is awake.

Accordingly in one aspect the invention may broadly be said to consist in a respiratory therapy system configured to supply breathing gases to a patient, the system comprising a controller configured to control the pressure of breathable gas delivered to the patient by a flow generator and to receive one or more signals from one or more sensors indicative of the pressure and/or flow of the gas in the system, wherein the system is configured to:

detect when the patient is inhaling and to control the flow generator to deliver breathable gas at an inspiration pressure (IPAP), detect when the patient is exhaling and to control the flow generator to deliver breathable gas at an expiration pressure (EPAP), the EPAP being lower than the IPAP, detect when the patient is at least one of awake and/or asleep, the system being further configured according to a back-up mode in which the system controls the flow generator to deliver a back-up breath, if inspiration is not detected within a predetermined back-up duration, or within a predetermined back-up rate, the system being further configured such that when the system detects that the patient is awake, the system alters the back-up mode.

In some examples, the system alters the back-up mode to disable, switch-off, deactivate or override the back-up breath, when the patient is awake.

A controller and/or method of providing respiratory therapy may be provided in accordance with any of the above aspects of the invention.

Further aspects of the invention, which should be considered in all its novel aspects, will become apparent from the following description.

DETAILED DESCRIPTION OF EMBODIMENTS

The invention relates to control of the breathing gas pressure supplied to a patient during respiratory therapy using a respiratory therapy system. The invention also relates to a method of controlling such a system, and to the system itself.

As background, such a system typically supplies a breathing gas flow generated by a blower, fan or flow generator which forces breathable gas along a gas delivery flow path, typically including a gas delivery tube, to the patient. The flow of breathable gas is delivered to the patient via a patient interface which seals around the nose, mouth, or both the nose and mouth of the patient. The pressure of the breathable gas that is supplied is controlled by a controller, usually using measurements taken from one or more pressure or flow sensors located along the gas flow path somewhere in the system, and either predetermined or automatic calculations based on those measurements. The pressure of the breathing gas flow that is ideal for the patient concerned may be set in advance by a clinician, or calculated by the system.

The controller may typically comprise one or more electronic controllers such as one or more microprocessors configured to receive a signal from a sensor, such as one or more pressure and/or flow sensors, and to subsequently control the pressure of the breathable gas flow in accordance with calculated, or predetermined pressure profile. In one example, the controller is configured to control the pressure by varying the speed of the blower.

The current invention is a development of bi-level (BPAP) pressure control where the pressure of breathable gas supplied to the patient switches between an inspiration pressure during inspiration (IPAP) and another, usually lower, expiration pressure during expiration (EPAP). Bi-level PAP control is known in the art and is described in patents U.S. Pat. Nos. 5,148,802, 5,433,193 and 5,134,995 the entire contents of each of which are incorporated herein by reference.

A bi-level respiratory therapy system typically detects the onset of inspiration, from data received from the one or more pressure and/or flow sensors in the system, for example in the gas delivery conduit and/or the patient interface and/or one or more connectors of the gas delivery conduit, and increases the pressure of the breathable gas delivered to the patient to the inspiration pressure (IPAP). The system typically further detects the onset of expiration and reduces the pressure of the breathable gas delivered to the patient to the, lower, expiration pressure (EPAP). The expiration pressure may be predetermined to be a fixed amount less than the delivered inspiration pressure and may therefore be considered to be expiratory pressure relief. The system may therefore be configured to automatically drop the pressure of the delivered gas by, for example, 2-4 cm $H2O$, once expiration is detected. A typical pressure difference between IPAP and EPAP when treating OSA would be about 3 cm $H2O$ for example. Any other suitable pressure difference between IPAP and EPAP may be selected as required. The inspiration pressure may be set in advance by the clinician, or by the clinician during set-up/titration of the system, or by the system controller in accordance with one or more predetermined algorithms and/or calculations.

As described in U.S. Pat. No. 5,148,802, bi-level may be applied in spontaneous mode (S-mode), in which the flow generator delivers breathable gas at an inspiration pressure (IPAP) on detection of inspiration, and at a lower expiratory pressure (EPAP) on detection of expiration. Triggering the change in pressure from EPAP to IPAP is based only on the detection of patient inspiration. Typically, there will be a maximum duration for which IPAP can last ($D_{max}$), so the system will not stay at IPAP in the event of a leak.

In spontaneous/timed mode (S/T mode), patient breathing will also trigger the change between EPAP and IPAP, but additionally a back-up breath is applied by the system if inspiration is not detected within a back-up duration or in accordance with a back-up rate. Typically, the back-up duration or back-up rate is set by a clinician. The back-up breath will typically have a set duration ($D_{set}$); that is, if the back-up breath is triggered, IPAP will be applied for $D_{set}$.

The current invention is also a development of a further development of bi-level respiratory therapy control whereby the pressure of breathable gas delivered to the patient by the respiratory therapy system is varied in dependence upon whether or not the patient is awake. Using this type of control, if the system detects that a patient wakes up, or is awake, during treatment, the supplied pressure of the breathable gas may be decreased, primarily to make the therapy more comfortable for the patient. Typically higher pressures can be used when the patient is asleep, without causing discomfort. This type of control is described in U.S. Pat. No. 6,988,994 the entire contents of which are incorporated herein by reference.

U.S. Pat. No. 6,988,994 describes a positive airway pressure respiratory therapy system and method for treatment of a sleeping disorder in a patient. The system includes a flow generator, one or more sensor(s) and a processing arrangement/controller which may be one or more electronic microprocessors. The generator supplies breathable gas to the patient so as to apply a pressure to an airway of a patient. The sensor(s) measures data corresponding to a patient's breathing pattern. The controller analyses the patient's breathing patterns to determine whether the breathing patterns are indicative of at least one of the following patient states: (i) a regular breathing state, (ii) a sleep disorder breathing state, (iii) a REM sleep state and (iv) a troubled wakefulness state. The controller adjusts the applied pressure as a function of the patient's sleep/awake state. Those skilled in the art will understand that the regular breathing state will include both an apnea free sleeping and a relaxed wakeful state of the patient, while the troubled wakefulness state is one in which anxiety to discomfort of the patient results in irregular breathing. The system thus detects the awake or sleep state of the patient and adjusts the pressure of the delivered gas accordingly.

We have proposed a bi-level respiratory therapy system and method which may incorporate a back-up measurement being a back-up time related variable such as a back-up time period/duration or back-up frequency/rate associated with the mode of therapy. The back-up time related variable is a clinician set time period which is set to try to correspond to the patient's breathing rate/breath duration. The system controller has a timer which compares the set back-up time related variable with corresponding time-related characteristic of the breath, such as for example, the actual duration of a breath. If a breath is not detected in accordance with the back-up time related variable, for example within the back-up duration, the system automatically tries to initiate a new breath by switching to the higher IPAP pressure. Effectively, the system times the patient's breathing rate and/or duration, and in particular the rate and/or duration of at least the expiratory portion of the breath and if the patient takes too long to take a breath, the system switches to IPAP to try to force the patient to start spontaneously breathing again.

Where the back-up time related variable measurement is a back-up rate, this corresponds to a breathing rate (essentially breath duration) which is set by the clinician. When a patient is breathing spontaneously with a breathing rate quicker than the set back-up rate (i.e. breath duration shorter than the "back-up duration") the system will oscillate between a clinician set IPAP and EPAP during inhalation and exhalation respectively. In this situation the back-up time related variable control methodology is not triggered. While breathing spontaneously, if a single breath duration exceeds the back-up duration then the system will automatically try to initiate a new breath by transitioning to the clinician set IPAP. This is intended to provide a guarantee that the system switches between IPAP and EPAP at a rate no less than the back-up rate when the patient is asleep. So for example if the patient takes a breath and inhales every 5 seconds, the back-up duration may be set at 6 seconds from the start of inspiration. If the back-up time related variable measurement is a back-up time period, the expiratory portion of the patient's breathing may be observed, measured or determined, to last on average 3 seconds. The back-up duration would then be set at 4 seconds from the start of expiration. The above example has been provided in terms of time duration, typically measured in seconds, but could alternatively be provided in terms of rate or frequency, typically measured as BPM.

When a patient is awake, having a back-up time related variable may be undesirable because, if the patient slows down their breathing or takes a long breath, the back-up time related variable control may trigger, delivering IPAP and providing discomfort. This is further compounded when a patient's resting breathing rate is slower than that which a clinician would like to guarantee during sleep (i.e. the set back-up duration or back-up rate), which may cause significant discomfort when the patient is awake, due to unwanted triggers to IPAP.

We therefore provide a bi-level respiratory therapy system wherein the controller incorporates control methodology configured to disable or switch off or deactivate or override the back-up time related variable control feature, when the patient is awake. So this involves detecting when the patient is awake and asleep, and also detecting when the patient inhales and when they exhale, and comparing the frequency and/or duration of inhalation to a predetermined back-up frequency and/or duration. The system is therefore configured to be able to detect when the patient is awake and asleep, and also to detect when the patient is inhaling (and when they are exhaling). Further the system is configured to include a timer which is used to measure the back-up time related variable, after which the system automatically applies IPAP if inspiration is not detected. If, in the circumstance where inhalation is not detected in accordance with the back-up time related variable, but the system also detects that the patient is awake, the system does not apply a back-up breath, and thus discomfort to the patient is minimised, even though the system has not detected a breath in accordance with the set back-up time related variable. The back-up time related variable is therefore either only set by the system when the patient is asleep, or is set for both when the patient is asleep and awake, but the automatic triggering to IPAP in the absence of inhalation is not activated if the system detects that the patient is awake.

The system or clinician may therefore measure the time period between the start and end of inspiration and the start and end of expiration. The system or clinician may then set the back-up signal to be a back-up duration being a desired amount of time longer than the measured time period. The measured time period may be for the total length of a breath cycle, that is, the total length of inspiration and expiration. It may be useful to base the measure time period on a selected portion of a patient's breath cycle, such as the expiratory portion. Alternatively, the system or clinician may measure how many times inspiration begins in a given time period to determine an inspiration rate or frequency. The back-up signal may then also be set to be a rate or frequency, which is lower than the breathing rate.

IPAP, EPAP and the back-up time related variable may be set by a clinician during set-up of the system with a given patient, or may be determined automatically by the system. The system may incorporate control methodology to automatically adjust the IPAP, EPAP and/or back-up time related variable in response to signals received from one or more pressure and/or flow sensors and/or other sensors in the system.

In some examples, the back-up duration may be intended to be longer than the maximum duration of the breath of a patient. Typically, a clinician will set the back-up duration to be longer than the typical breath of a patient so that, when awake, the patient does not feel "pushed along" by IPAP being prematurely triggered by the back-up duration that has been set. However, if the back-up time related variable is not applied when the patient is awake the need for this is removed. The clinician is therefore free to set the back-up duration to be shorter, the same as, or longer than the typical breath duration, depending on the therapeutic outcome desired. For example, a shorter back-up duration may be set so that the patient's ventilation is increased, or a similar or slightly longer back-up duration may be set if the clinician wants to ensure the patient breathes at, or no slower than, a particular rate.

The above described system, method and controller may be configured to adjust the back-up time related variable upon detection that the patient is awake, rather than fully disabling the back-up time related variable. For example, instead of disabling the back-up time related variable, it is envisaged that the system could increase the back-up duration during an awake state such that, in practice, the IPAP would not be prematurely triggered. Adjusting the back-up time related variable such that the back-up duration is lengthened when the patient is awake may be preferable over disabling or disengaging the back-up duration altogether, as in the event that the system mistakenly detects that the patient is awake when the patient is actually asleep a back-up breath is still able to be applied.

It is also envisaged that further, or different, bi-level control settings could be varied while the patient is sleep or awake. Examples are set out below:

a) Pressure support could be generally reduced, during IPAP and/or EPAP when the patient is asleep to provide increased comfort in some patient groups such as those suffering from OSA. Pressure support could be generally increased, again during IPAP and/or EPAP, in other patients such as those suffering from OHS to increase ventilation when they are hypoventilating while asleep.

b) IPAP/EPAP could be lowered when patient is awake to increase comfort by not subjecting them to higher therapeutic pressures. Alternatively, some patients might be used to the higher pressures and might find the lower pressures uncomfortable.

c) $D_{max}$, or the maximum amount of time the system may provide the IPAP pressure, could be over-ridden if the patient is awake, for example to make it more comfortable if a patient takes an extra deep breath. This would help to avoid patient discomfort if the pressure drops due to $d_{-max}$ while the patient is still inhaling and awake.

d) In some cases, IPAP and/or EPAP could be generally lower when it is detected that the patient is awake than when the patient is asleep.

e) The pressure difference between IPAP and EPAP could be different when the patient is asleep than when they are awake. For example there could be a greater pressure difference when the patient is awake, for comfort during expiration.

A further variant is also envisaged in which the system is configured to deliver CPAP to the patient when the patient is awake, rather than varying the pressure between IPAP and EPAP when the patient is awake. Such a variant would use the same back-up time related variable methodology as described above, but only switch between IPAP and EPAP when the patient is detected as being asleep. The CPAP would preferably be lower than at least IPAP, and may also be lower than EPAP.

Unless the context clearly requires otherwise, throughout the description, the words "comprise", "comprising", and the like, are to be construed in an inclusive sense as opposed to an exclusive or exhaustive sense, that is to say, in the sense of "including, but not limited to".

Although this invention has been described by way of example and with reference to possible embodiments thereof, it is to be understood that modifications or improvements may be made thereto without departing from the scope of the invention. The invention may also be said broadly to consist in the parts, elements and features referred to or indicated in the specification of the application, individually or collectively, in any or all combinations of two or more of said parts, elements or features. Furthermore, where reference has been made to specific components or integers of the invention having known equivalents, then such equivalents are herein incorporated as if individually set forth.

Any discussion of the prior art throughout the specification should in no way be considered as an admission that such prior art is widely known or forms part of common general knowledge in the field.

The invention claimed is:

1. A respiratory therapy system configured to supply a breathable gas to a patient, comprising:

a flow generator configured to deliver the breathable gas to the patient via a patient interface;

one or more sensors, each sensor configured to detect a pressure or a flow of gas from within the patient interface and to generate one or more signals corresponding to the pressure or the flow of gas from within the patient interface; and a controller configured to receive and analyze the one or more signals from the one or more sensors to determine when the patient is inhaling or exhaling, and to determine when the patient is awake or asleep, and to control the flow generator to deliver the breathable gas at:

(i) an inspiration pressure (IPAP) when the controller determines that the patient is inhaling, (ii) an expiration pressure (EPAP) when the controller determines that the patient is exhaling, the EPAP being lower than the IPAP, wherein the controller is further configured to receive or generate a back-up time related variable and to compare a time related variable of at least a portion of a breath of the patient with the back-up time related variable, and to automatically control the flow generator to deliver a back-up breath in which the breathable gas is delivered to the patient at the IPAP for a first predetermined time when the controller determines that the patient is not inhaling in accordance with the back-up time related variable, wherein the controller is further configured to control the flow generator to vary a maximum value (Dmax) for an amount of time breathable gas is provided to the patient at IPAP when the controller determines that the patient is inhaling, wherein Dmax varies based on a determination by the controller that the patient is awake, and wherein the controller is further configured to override delivery of the back-up breath when it is determined by the controller that the patient is awake.

2. The system of claim 1, wherein the back-up time related variable is a back-up duration corresponding to a length of time of a breathing parameter.

3. The system of claim 2, wherein the controller is further configured to control the flow generator to not deliver the breathable gas at the IPAP to the patient when the controller determines that the patient is not inhaling after the back-up time duration has passed and the controller determines that the patient is awake.

4. The system of claim 3, wherein the back-up duration is any one or more of:

a) greater than a maximum length of all of, or a portion of, the breath of the patient, b) less than the maximum length of all of, or a portion of, the breath of the patient, and c) substantially the same as the maximum length of all of, or a portion of, the breath of the patient.

5. The system of claim 1, wherein the back-up time related variable is a back-up rate corresponding to a back-up time frequency at which a breathing parameter, a portion of the breath, or the complete breath, of the patient occurs.

6. The system of claim 5, wherein the controller is further configured to control the flow generator to not deliver the breathable gas at the IPAP to the patient when the controller determines that the patient is not inhaling at a frequency slower than the back-up time frequency and the controller determines that the patient is awake.

7. The system of claim 5, wherein the back-up rate is any one of:

a) less than a frequency of all of, or a portion of, the breath of the patient, b) greater than the frequency of all of, or a portion of, the breath of the patient, and c) substantially the same as the frequency of all of, or a portion of, the breath of the patient.

8. The system of claim 1, wherein the back-up time related variable is generated by the controller based on a typical breath of the patient, or an inspiratory or an expiratory portion of the typical breath.

9. The system of claim 1, wherein the controller is configured to disable the back-up time related variable when the controller determines that the patient is awake.

10. The system of claim 1, wherein the controller is configured to adjust the back-up time related variable when the controller determines that the patient is awake.

11. The system of claim 10, wherein the back-up time related variable is a back-up duration, and the controller is further configured to increase the length of the back-up duration when the controller determines that the patient is awake, such that the back-up duration is longer than a typical length of the breath of the patient.

12. The system of claim 1, wherein the controller is further configured to control the flow generator to deliver the breathable gas at a lower pressure when the controller determines that the patient is awake than when the controller determines that the patient is asleep.

13. The system of claim 1, wherein a pressure difference between the IPAP and the EPAP is different when the controller determines that the patient is awake as compared to when the controller determines that the patient is asleep.

14. The system of claim 13, wherein the pressure difference is greater when the controller determines that the patient is awake.

15. The system of claim 1, wherein when the controller determines that the patient is awake, then one of a) a maximum duration of IPAP is disabled, b) the maximum duration of IPAP is increased, and c) the maximum duration of IPAP is overridden.

16. The system of claim 1, further comprising any one or more of the following:

a) a humidifier configured to increase humidity of the breathable gas delivered to the patient and b) a gas delivery tube between the flow generator and the patient, wherein the tube is configured to be heated.

17. The system of claim 1, wherein the controller is further configured to control the flow generator to deliver the breathable gas to the patient when the controller determines that the patient is not inhaling in accordance with the back-up time related variable and the controller determines that the patient is awake, such that CPAP is delivered to the patient, when the controller determines that the patient is awake.

18. The system of claim 1, wherein the controller is further configured to control the flow generator to deliver the breathable gas to the patient when the controller determines that the patient is not inhaling in accordance with the back-up time related variable and the controller determines that the patient is awake, and wherein the back-up time related variable when the controller determines that the patient is awake is different from when the controller determines that the patient is asleep.

19. The system of claim 1, wherein the controller is further configured to control the flow generator to vary a set duration (Dset) that the breathable gas is delivered to the patient at the IPAP when the controller determines that the patient is not inhaling in accordance with the back-up time related variable, and the controller determines that the patient is awake.

20. The system of claim 19, wherein when the controller determines that the patient is awake, then one of:

a) the set duration of IPAP is disabled, b) the set duration of IPAP is increased, and c) the set duration of IPAP is overridden.

\* \* \* \* \*